United States Patent
Li et al.

(10) Patent No.: US 11,040,123 B2
(45) Date of Patent: Jun. 22, 2021

(54) AIR PURIFICATION SYSTEM

(71) Applicants: Dong Li, San Ramon, CA (US); Ge Yi, San Ramon, CA (US)

(72) Inventors: Dong Li, San Ramon, CA (US); Ge Yi, San Ramon, CA (US)

(*) Notice: Subject to any disclaimer, the term of this patent is extended or adjusted under 35 U.S.C. 154(b) by 111 days.

(21) Appl. No.: 16/592,775

(22) Filed: Oct. 4, 2019

(65) Prior Publication Data
US 2021/0100924 A1 Apr. 8, 2021

(51) Int. Cl.
*A61L 9/20* (2006.01)
*B01D 53/88* (2006.01)
*A61L 9/014* (2006.01)
*B01D 53/00* (2006.01)

(52) U.S. Cl.
CPC ............ *A61L 9/205* (2013.01); *A61L 9/014* (2013.01); *B01D 53/007* (2013.01); *B01D 53/885* (2013.01); *A61L 2209/111* (2013.01); *A61L 2209/12* (2013.01); *A61L 2209/14* (2013.01); *A61L 2209/22* (2013.01); *B01D 2255/2047* (2013.01); *B01D 2255/20707* (2013.01); *B01D 2255/20715* (2013.01); *B01D 2255/20776* (2013.01); *B01D 2255/20792* (2013.01); *B01D 2255/802* (2013.01); *B01D 2257/91* (2013.01); *B01D 2259/804* (2013.01)

(58) Field of Classification Search
None
See application file for complete search history.

(56) References Cited

U.S. PATENT DOCUMENTS

| | | | | |
|---|---|---|---|---|
| 5,961,920 A | * | 10/1999 | Soremark | A61L 2/10 210/760 |
| 2003/0206840 A1 | * | 11/2003 | Taylor | B03C 3/12 422/186.04 |
| 2006/0283786 A1 | * | 12/2006 | Harbers | B01J 19/123 210/85 |
| 2010/0183476 A1 | * | 7/2010 | Lu | A61L 2/18 422/21 |
| 2014/0227140 A1 | * | 8/2014 | Engelhard | A61L 9/20 422/121 |
| 2016/0038624 A1 | * | 2/2016 | Krosney | A61L 9/20 422/121 |
| 2020/0009286 A1 | * | 1/2020 | Zarcone | A61N 5/0618 |

* cited by examiner

*Primary Examiner* — Jelitza M Perez

(57) ABSTRACT

A portable or handhold air cleaning system, whose air flow pipeline made of highly reflective and low absorptive material for UVC or UVB light acts also as a UV light waveguide, is invented. The system features a TEC cooled LED light source; air flow warm up mechanism; and UV light absorption/air cleaning enhancement device. The system is useful for travellers and office workers during flu and hay-fever seasons.

19 Claims, 3 Drawing Sheets

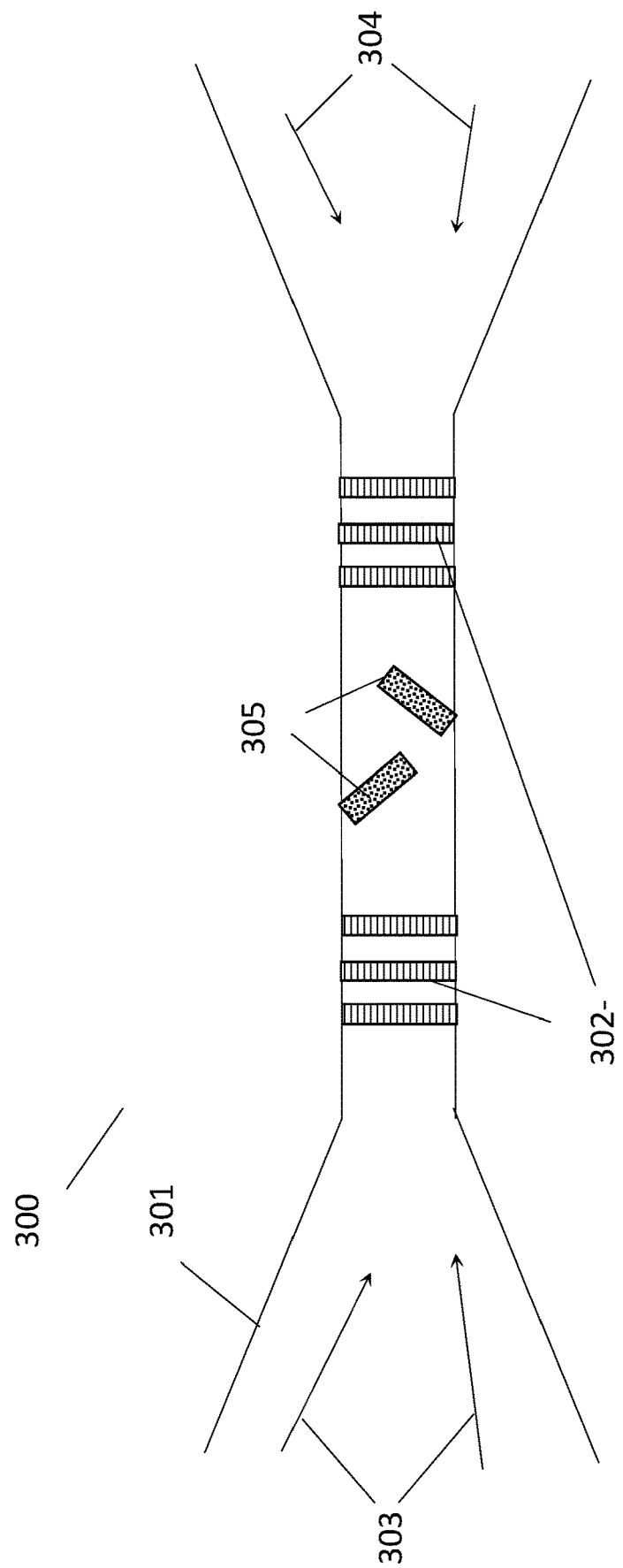

AIR PURIFICATION SYSTEM

FIELD OF INVENTION

Figure 1:
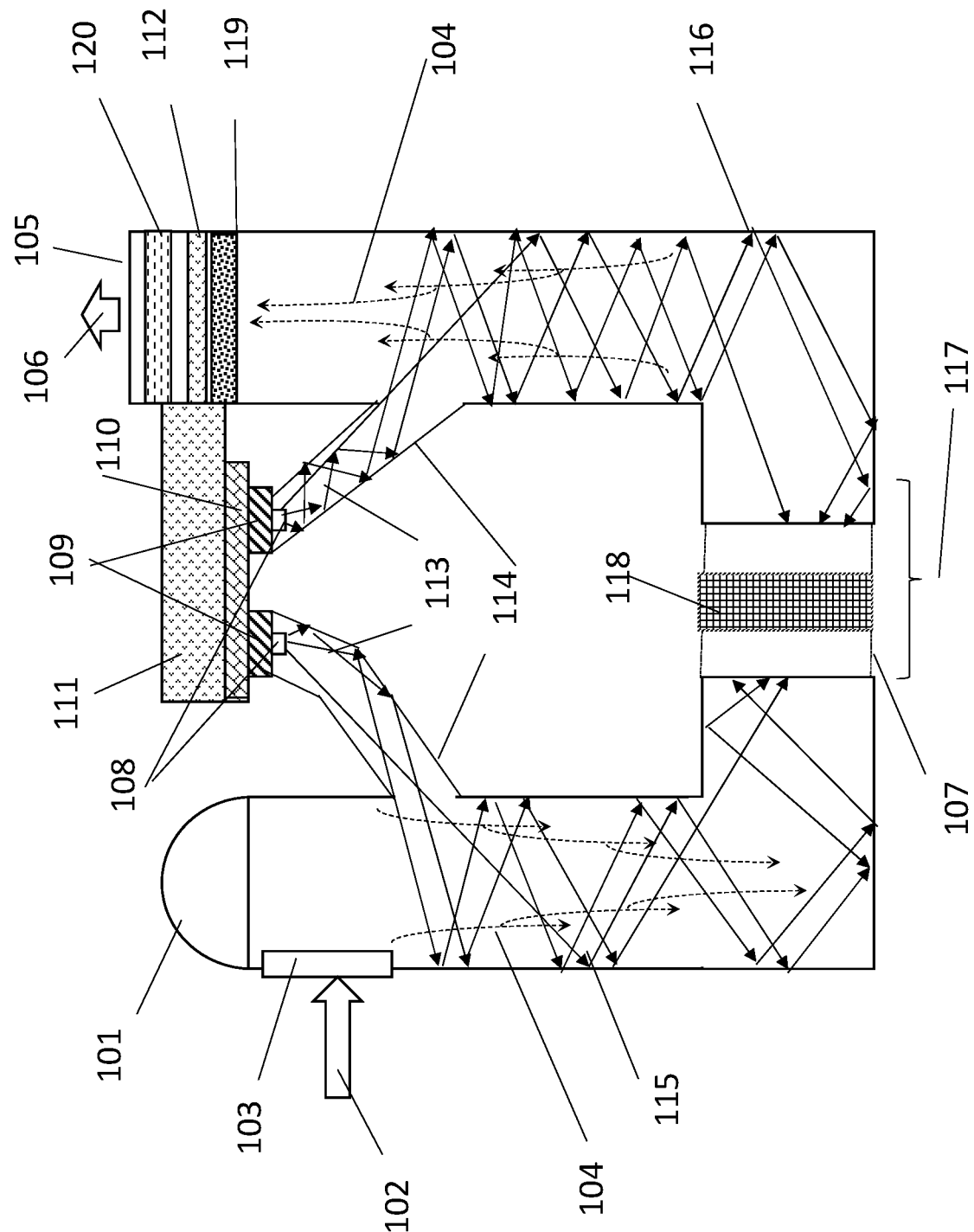

The invention is related to air purification system. Particularly, a portable or handhold air supply system to provide sterilized air flow to its users.

BACKGROUND ART

To keep a human being alive, he or she needs take enough energy from food by eating, and also obtain enough oxygen and get rid of carbon dioxide by breathing. A person may keep himself/herself alive life without taking food for a few days but cannot survive more than a few minutes without breathing. Just as eating a heathy food, taking in "heathy" air is extremely important to our life quality.

Unfortunately, air can carry quite a lot of pollutants, namely bioaerosols, such as bacteria, mold, viruses, endospores, and even pollen, which can trigger various of infections, allergy and asthma reactions. Some of them can even ultimately lead to complicated short term or long term heath issues. For example, flu is among the top causes of death every year, particularly for the elderly.

It has been a long time effort for scientists and engineers to find an affordable solution to provide healthier air to ordinary people. Currently, there are a few air purification methods, each of which will be discussed in the following sections.

Physical filtering is one of the simplest method and used on quite some systems on the market. It implements a high-efficiency particulate air (HEPA) filter in the systems to take out particles larger than certain size out of the air flow. However, there are some disadvantageous for such system. Firstly, it has been shown particles with size smaller than 300 nm (or 0.3 um) can pass through the HEPA filter. Unfortunately a lot of pollutants below 0.3 um do exist. Further reducing the size of filter will increase the cost of the filter dramatically and also impeach the smoothness of air flow through the filtration system. Secondly, experiments found that the organic pollutants caught on the filter can even grow on the filter surface and reenter into the air stream.

Another air cleaning system is based on ozone oxidation. Ozone generators were once used as an air cleaning method. However, the later studies show clearly that it could do more harm than good to human body particularly to our respiratory system. It has been scientifically proven that breathing ozone is part of root cause of asthma and need to remove totally from the air we take in.

Photoelectrochemical oxidication (PECO) is a relatively new commercially available technology used for air cleaning. It uses filters coated with nano particles of titanium dioxide TiO2, which, in the presence of water and under radiation of UVA light (UV light with wavelength 315-400 nm), can produce hydroxyl radicals and super-oxide ions to oxidize the organic contamination into volatile organic compounds (VOCs), and eliminate micro-organisms adsorbed on the catalyst surface. It is claimed that the PECO systems can remove particles as small as 0.1 um.

The semiconductor catalyst (TiO2) assisted photoelectrochemical reactions occur as below:

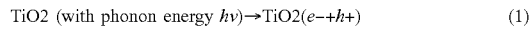
(1)

(2)

(3)

(4)

(5)

The PECO system shows a number of pathways for the production of oxidative species that facilitate the oxidation of the organic species, RX, in addition to its direct oxidation by the excited TiO2 itself. To enable the air cleaning, the organic species RX need to contact the surface of the TiO2 to engage to either itself or any oxidative species to make things work, which is not a very efficient way for a consistently running air flow. It is also quite clear that water molecule in the air play a crucial part in these reactions. For air with low humidity, such as air in airplane (usually humidity less than 20%), the reactions described above are much less efficient. Moreover, to make things work, it still need the physical filter. Virus (size as small as ~20 nm) below 0.1 um can pass through and escape from the PECO air cleaning system.

Germicidal UV-C (UVC, also named as far UV or deep UV light with wavelength 180-280 nm) and UV-B (or UVB with wavelength 280-315 nm) can be used for air cleaning. The UVC and low wavelength UVB can make damage on protein in virus and prohibit its reproduction activity. UVC and UVB light can even efficiently inactivate organic bioaerosols such as multi-drug-resistant bacteria, differing strains of viruses. The basic theory behind this application is that the UVC and low wavelength UVB can deactivate pathogenic bacteria, viruses and other microorganisms via formation of thymine dimers in deoxyribonucleic acid (DNA), which prevents further replication of the DNA strain. It is worth to note that the maximum absorption wavelength of DNA or RNA is approximately 260 nm, therefore UVC is much more efficient than UVB.

The widespread use of germicidal ultraviolet light in public settings has been very limited because UV light, particularly UVB, UVA and high wavelength UVC light, are a human health hazard, being both carcinogenic and cataractogenic. Secondly, the conventional UVC sources, which are the most efficient one for germicidal purpose, are Low- or medium-pressure mercury vapor lamps with a high operating voltage on the order of 1-10 kV, and a high-power UV radiation (on the order of 10 W) at a wavelength of 254 nm-close to 260 nm, which are not for the portable, particularly for handhold devices. There are many drawbacks to using mercury vapor lamps; for example, the lamps contain highly toxic mercury sealed in a fragile quartz glass tubes, which is easy to break and contaminate the environment. The lamps have a long warmup times of approximately 10 min.

Deep-ultraviolet, i.e. UVC, light-emitting diodes (DUV-LEDs, UVC LEDs), a solid light source based on carrier injection into multiquantum well (MQW) semiconductor layer, has numerous advantages and may provide solutions to the above drawbacks of UV mercury lamps for portable and handhold air cleaning devices. Two materials systems provides most promising working devices—AlGaN, and InGaN. Despite of a lot of progress for AlGaN DUV LED systems, such as achieving a narrow emission spectrum which is tunable between 210 nm (AlN) to 365 nm (GaN), a low operating voltage of the order of DC 10 V, and instantaneous operation, most commercially available DUV LED is still based on InGaN with wavelength at the high boundary of DUV (ie. 265-285 nm). Another issue of existing DUV LED is its really low external quantum efficiency (only a few % for the time being), which means that, to achieve high output power, a significant input power needed with majority of power turning into heat. This demands a solution for quick heat dissipation. On the other hand, UVC LED is much more suitable for handhold air cleaning devices.

It is not easy to make a UVC LED working on a handhold air purification device. One one hand, considering UVC LED's low output efficiency and challenge on heat dissipation for keeping the device alive, only UVC LED with output power of a few mW can be used on the portable or handhold system. On the other hand, to make air cleaning work, the bioaerosols need to expose under enough UVC dosage or enough accumulated light energy to trigger the dimmer formation. This puts forward a great challenges on system designers to answer the question—how to use the lower output UVC LED to provide enough energy exposure to terminate the DNA's reproduction in the incoming bioaerosols within the air stream.

The invention proposed here provides a solution for this dilemma for portable or handhold air cleaning device based on UVC and/or UVB LED.

SUMMARY OF THE INVENTION

In this invention, we proposed a design for a portable or handhold air cleaning device based on the UVC and/or UVB LED.

The concept of this invention is to use the high UVC and/or UVB reflection (>75%) and low UVC and/or UVB absorption material at least on the internal surface of air supply pipeline, whose internal surface acts also as a UV light waveguide. By doing so, it provides enough UVC and/or UVB light exposure to deactivate all the incoming bioaerosols in the supplied air, therefore offers a cleaned air stream to its user.

The design principle of the proposed system is to allow everything in the air flow through the system, from the air inlet to the air outlet, to experience maximum UV exposure. As such, we add UV photon entanglement block(s) within the air flow pipeline (also UV waveguide) to locally further boost the UV area density (dosage) as well as reduce the air flow speed to provide more UV exposure for everything in the incoming air flow. In one design, several UV reflector, also acting as air flow speed buffer, are built in the air flow pipeline using the highly reflective material to provide either a further enhancement for the UV exposure time or reflect the UV light back to the system for the safety of the its user. In another design, porous highly UV reflective materials is chosen to act as UV entanglement block and air flow speed buffer.

Moreover, a new plamonic feature or several features with electrical isolated metal nano-particles (NP) on top of the high UV reflective substrate, are added inside the air flow pipeline to further enhance the cleaning functionality. The incoming UV light will induce plasmonic resonance in the metal nano particles, to either generate the plasmon induced heating or re-emit enhanced UV light around the NP at the interface between the NP and air. Several materials, such as Al, Ga, Rh will be used for such purpose. The plasmonic feature is also used at the air outlet of the system to provide UV absorption as well as air heating before the air supplied to its user(s).

In another design, device with TiO2 or ZnO nano particles on a either solid or porous highly UV reflective materials is introduced to provide further air cleaning based on either photocatalytic reactions or PECO when there is enough moisture in the incoming air. This also help to absorb the UV light at the middle point of air flow path.

The plasmonic feature(s) and UV photon entanglement blocks will be placed around the middle point of the air flow path so that UV light, injected from both the air inlet side and the air outlet side can interact with them.

Considering the UV light interacting with oxygen in the air could potentially generate some small amount of ozone, the system also implements an activated carbon filter near the air outlet inside the air flow pipeline purely for the purpose of removing the small amount of ozone from air supply to its user.

To provide cooling to the UVC and/or UVB LED, we implement a thermal electrical cooler (TEC) with a heat sink, whose higher temperature end is placed near the air outlet outside the air flow pipeline to warm up the output air above the ambient temperature, which provides an expelling force to the ambient air. This helps to create an air supply system to ensure the air reaching to its user is the purified air from the system rather from the surrounding environment.

Our portable and/or handhold air cleaning system is very useful for travelers in the closed environment such as in an airplane, or on a train. It can also use in office during flu season particularity for the elderly as well as provide cleaned air for users against the hay-fever.

BRIEF DESCRIPTION OF THE DRAWINGS

FIG. 1 a schematic embodiment of the portable or handhold system proposed in this invention to use UVC or UVB LED for air purification.

FIG. 2 one of the embodiment of UV photons entanglement structure also acting as an air flow buffer.

FIG. 3 an embodiment of another design with air flow path reduction, UV entanglement structure and plasmonic feature in the system.

DETAILED DESCRIPTION

The following numerous specific detail descriptions are set forth to provide a thorough understanding of various embodiments of the present disclosure. It will be apparent to one skilled in the art, however, these specific details need not be employed to practice various embodiments of the present disclosure. In other instances, well known components or methods have not been described.

FIG. 1 shows a schematic embodiment of the proposed handhold system in this invention. As mentioned previously, the design principle of the proposed system is to allow everything in the air flow to experience maximum UV exposure from the air inlet to air outlet by using the air flow pipeline as a UVC/B light waveguide based on the reflection from the internal surface of the air pipeline made of UVC/B highly reflective and low absorption material(s). For the purpose of simplicity, in FIG. 1, only the internal surface of the air pipeline is shown and represented here. Having said that, the highly UVC/B reflective material for internal surface of the air flow pipeline and the body of the air flow pipeline can certainly be the same materials such as Polytetrafluoroethylene (PTFE). As shown, the whole air pipeline at least the internal surface made of highly UVC/B reflective material has a sealed end indicated here as 101. Ambient air 102 shown here as a arrow is taken into the system from the air inlet with an air filter 103 either from an air pump or a blow-in fan. The air filter built in the air inlet is just a low grade filter to prevent dust in the air into the system. The air flow inside the system shown here as 104, represented by the broken lines, goes through the whole air flow pipeline and reach to the air outlet 105 indicated by another arrow 106. The whole air flow pipeline presented here as a U shape with the dotline 107 indicating that the whole pipeline can be much longer than what is being shown here.

The light injection into the system is from two UVC/B LEDs 108. For the simplicity of drawing, two UVC/B LEDs are shown here. Nevertheless, a single LED can certainly be used in the system with proper design of the reflection from the internal surface of the waveguide for splitting the beam (batch of light) from one LED into two similar paths as indicated here in FIG. 1. In fact, using one UV LED saves power and make the heat dissipation relatively easier, which is particularly important for handhold device. Nevertheless, with main power outlet available on modern airplanes and trains, even for personal handhold air purification device, power may not be a limited factor here. The UVC/B (much more preferable UVC due to the main DNA absorption peaking at 260 nm) LED(s) 108 sits on its own package mostly with a heat sink 109. A thermoelectric cooler TEC 110 is used and mounted over the LEDs's own heat sink 109 to assist the heat dissipation of the LED 108. The TEC is also thermally connected to its own heat sink 111, which also links to a heat spreader/radiator 112 surrounding and being out the air flow pipeline. The heat spreader/radiator 112 helps to warm up the air 106 out from the air outlet 105, which helps to provide warmer air than that of ambient air to the user. The warmer air also has a higher pressure than that of the ambient air therefore provide an expel force pushing the colder ambient air away from the user and makes the post-purified air from the system become the solo air source for the user(s).

The UVC/B light 113 emitting from the LED 108 is also surrounded by UVC/B waveguide 114 made of UVC/B highly reflective materials with low light absorption, and is guided and split into the air inlet branch and air outlet branch to purify the air flow 104 at both branches. The batch of arrows 115 indicated the UVC/B, at the air inlet branch, bounced by the internal reflection of the waveguide 114 and the internal surface of air flow pipeline 101 while the branch of arrows 116 indicated those at the air outlet branch experience similar reflection. It is worth to note the two branch of arrows or UV light will eventually meet around the middle point of the air flow path 117. Near the middle point of the air flow path 117, there are some special structures and or functional features to further enhance the air purification and cleaning, which will be discussed in the following sections.

As shown in FIG. 1, near the air outlet 105, there are also a couple of functional features: 119 is a plasmonic device made of UVC/B highly reflective material, on which there is specially fabricated electrically isolated metal nano particles being able to generate plasmonic resonance at the UVC and low UVB wavelength; near the air outlet 105, 120 is an activated carbon filter, whose function is to remove any trace of ozone, which could be produced or already existing in the incoming air flow. It also help to remove any odor, if there is any, from the incoming air flow and it is the last safeguard before the purified air reaching its user(s).

There are quite a few choice of materials for UVC/B with high reflection and low absorption. They are general PTFE film or tube (eg. those from Gore); or ePTFE (expanded PTFE) film or tube; or porous PTFE film or tube; film of Nitrocellulose; or even Nitrocellulose pain with special components (without those for high UVC/B absorption); Teflon® tape/film and tube; Aluminum foil or tube; Tetratex® film or tube from Tetratec Corp (with its main composition as ePTFE); 3M™'s enhanced spec reflector (ESR) film/sheet (made of multi-layer polymer); Dupont™'s Tyvek® paper (made of high density polyethylene fibers) or Melinex® film/sheet (polyester); or Toray's Lumirror™ sheet (polyester).

For material used for the plasmonic device, nano particles in the size range from 5 nm-100 nm from Aluminium (Al) with AlOx, Ga, even more expensive Rh, or their combinations as an alloy system or an composite system for plasmonic resonance within UVC/B wavelength.

Figure 2:
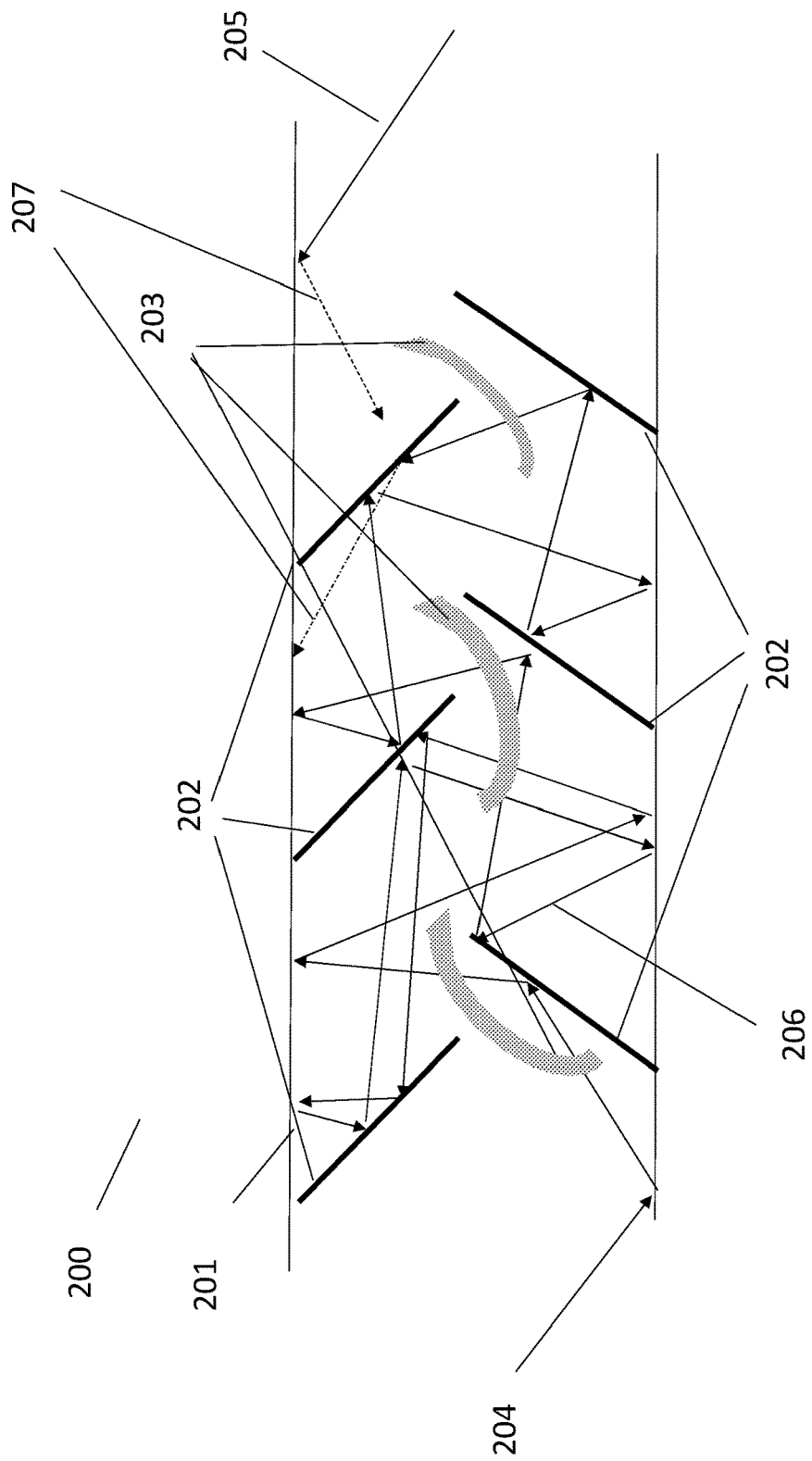

FIG. 2 shows one of the embodiment of cross-section view for the UV photons entanglement structure also acting as air flow buffer shown as 118 near the middle point of the air flow path 117 in FIG. 1. In this specially designed structure in the pipeline 200, just as shown in FIG. 1, the internal surface of the air pipeline 201 is made of highly UVC/B reflective and low UVC light (and/or UVB light) absorption materials, the structures 202 are planes also made of highly reflective and low UVC light (and/or UVB light) absorption materials, which is inserted into the air flow pipeline. The arrangement of the planes 202 still allows the air flow 203 to pass from left to right in this particular illustration but it will slow down the air flow speed to allow more dwell time of the air flow in this area. The incoming bounced UV light from left 204 and from right 205 all will be reflected multiple times, as represented by the solid arrows, by these planes at various locations while they try to find a way proceed. The dot lines of 207 indicates that the reflection will continue till all the light energy is fully absorbed by the materials during the propagation of UVC/B light in the air flow pipeline or absorbed by any pollutant or bioaerosols in the air flow. The whole structure 200 allows air flow and tangled UVC/B photons interact more thoroughly therefore effectively increase the opportunity of UVC/B exposure for any pollutant in the air flow. For any pollutant in the air flow, the overall UVC/UVB dosage which it exposes is the total UVC/B light it experiences after it gets into the system at air inlet before it gets out at the outlet. The longer it stays within the air pipeline, the higher the local UVC/B light intensity is, the higher the dosage it will see for any pollutant in the air stream. The structure 200 literally acts as a local UV light enhancement features via light entanglement (also with air flow) due to the reflection as well as extend the time for any pollutant exposed under the UV light.

FIG. 3 shows an embodiment of another design with cross section reduction of the air flow path, UV entanglement structure, and a plasmonic feature near the middle point of the air flow path 117 in FIG. 1 in the system. The design 300 has the internal surface of the air pipeline 301 made of highly UVC/B reflective and low UVC (and/or UVB) light absorption materials. As shown, the cross section of the air flow pipeline 301 is larger at the both ends and smaller in the middle of air flow pipeline. As such, the air flow is forced to reduce it cross section dimension while the air flow speed gets increased. The increase of air flow speed helps the flow go smoothly through the feature 302, which is made of either thin film with pass through channels with predetermined size (eg. certainly larger than 320 nm—upside of the UVC/UVB wavelength) or porous films of the highly reflective materials for UVC/B beams (batch of light) from both left 303 and right 304. The channels size varies in such a way that the closer to the center, the smaller the size. The ideas is that the air can flow through the the channels with greatly reduced cross section while the UVC/B photons can pass through the channels but get entangled in this areas due to multiple reflection induced light bouncing to provide more interactions with any pollutant in the air flow. Therefore, this provides chance for any pollutant to see more UVC/B dosage when it goes along with the air flow from air inlet to the outlet. The longer the UVC/B LED is on, the higher the intensity of the UC/B light within the feature 302. As shown in FIG. 3, there is another devices 305, which locates near the middle of the air flow path. It is arranged similar as what has been shown in FIG. 2.

In one case, the device 305 is made of electrically isolated metal nano particles (NPs), which can generate plasmonic resonance at the wavelength of UVC/B, deposited on highly UVC/B reflective film or substrate. The incoming UVC/B light will generate plasmonic resonance within these NPs, which can either heat up the NPs (plasmonic photothermal effect) or produce enhanced UVC/B light (plasmonic light enhancement effect) at the interface between the metal NPs and air. Metals such as Al, Ga, Rh, or their combination either as an alloys or a composite is capable of doing such tricks. Photothermal effect can raise the local temperature to significant high enough to deactivate some organic materials while the light enhancement effects products much stronger UVC/B light around the edge particularly the sharp corner of metal NPs (as antennas), which can boost local UVC/B dosage dramatically.

In another case, photocatalyst NPs, such as Titanium dioxide ($TiO_2$), or Zirconium oxide (ZrO), or Zinc oxide (ZnO), or Magnesium oxide (MgO), or tungsten trioxide ($WO_3$), or the combinations of the above mentioned photocatalyst along with or without small amount of addition of precious metal such as Pt, Au, Ru, Rd, Rh, is deposited on UV highly reflective and low UVC/B absorptive solid film or porous film. The UVC/B induced photocatalyst effect (if the incoming air is dry) or PECO effects (if the incoming air has high moisture) can further assist the air purification for the system. It is worth to note that our proposal here is different from the normal PECO systems in the market, which uses UVA light and also the catalyst particles is deposited on air filter(s). Here, the proposal catalyst is deposited on high UVC/B reflective and low UVC/B absorptive substrate to enhance the interaction between the photons and NPs of photocatalyst. Also the designed system expect to work well for dry air with low humidity based on photocatalyst effect alone.

What is claimed is:

1. A portable or handhold air purification system comprises at least:
   An air flow pipeline, with an air inlet and an air outlet, which carries an air flow taken from ambient air and is made of or its internal surface is made of a highly reflective material with low light absorption for ultraviolet c-band (UVC) and/or ultraviolet b-band (UVB);
   An ultraviolet c-band light emitting diode (a UVC LED) or a ultraviolet b-band light emitting diode (a UVB LED) as a ultraviolet light source emitting a batch of light into the air flow pipeline, inside which the air flow is cleaned via a ultraviolet light exposure; and
   A thermoelectric cooler (TEC) attached on said ultraviolet light source and mounted on a heat sink to keep the working temperature of the ultraviolet light source within a predetermined safe range via an accelerated heat dissipation.

2. The system of claim 1, wherein said batch of light emitted from said ultraviolet light source first passes through an ultraviolet light waveguide, which is made of a highly reflective material with low light absorption for ultraviolet c-band and/or b-band before injected into said air flow pipeline.

3. The system of claim 2, wherein said ultraviolet light waveguide is split a least into a couple of light paths—one for light injection near the air inlet, the other for light injection near the air outlet, to increase light exposure time and dosage for everything through the air flow pipeline.

4. The system of claim 1, wherein said air flow pipeline has an air path middle point, around which there is at least an extra feature, which is made of or whose surface is made of a highly reflective material with low light absorption for UVC and/or UVB, inside said air flow pipeline to further assist purification of said air flow through interaction with said batch of light.

5. The system of claim 4, wherein said extra feature is a group of planes, which partially block the air flow to act as an air flow buffer and reflect an incoming UV light from their surface to form an area with a light entanglement with the air flow.

6. The system of claim 4, wherein said extra feature is a group of planes which partially block the air flow and has a layer of photocatalyst nano particles absorbing a batch of incoming UV light to clean the air flow via either a photocatalytic effect or a photoelectrochemical oxidization effect.

7. The system of claim 1, wherein said air flow pipeline further comprises at least a device made of a group of inserted planes, on which there is at least a layer of electrically-separated nano particles of a metal for generating plasmonic resonance to either locally raise temperature high enough via plasmonic photothermal effect or produce an enhanced UVC and UVB light locally via plasmonic light enhancement effect, to assist the purification of said air flow.

8. The system of claim 7, wherein said group of inserted planes are made of or whose surface is made of a highly reflective material with low light absorption for UVC and/or UVB.

9. The system of claim 7, wherein said metal is either Al, or Ga, or Rh, or Mg, or Ag, or the combination of above mentioned metal either as an alloy or a composite.

10. The system of claim 7, wherein said device is placed either around a middle point of the air flow pipeline and/or near the air outlet inside the air flow pipeline.

11. The system of claim 1, wherein said heat sink for said TEC thermally connects to a heat radiator outside the air flow pipeline to raise the temperature of the air flow coming out from the air outlet above that of ambient air, which provides an expel force to surrounding ambient air.

12. The system of claim 11, wherein said expel force to surrounding ambient air keeps untreated ambient air away and leaves a user of the system with only a steam of purified air.

13. The system of claim 1, wherein said air flow pipeline has an activated carbon filter near said air outlet inside said air flow pipeline to remove a trace amount of ozone in said air flow before reaching said air outlet.

14. The system of claim 1, wherein said highly reflective material with low light absorption is either PTFE film and/or PTFE tube; or ePTFE (expanded PTFE) film or tube; or porous PTFE film or tube; or Nitrocellulose film; or low UV absorption Nitrocellulose paint; or Teflon® tape/film and/or Teflon® tube; or Aluminum foil and/or tube; or Tetratex® film and/or Tetratex tube from Tetratec Corp (with its main composition as ePTFE); or 3M™'s enhanced spec reflector (ESR) film/sheet (made of multi-layer polymer); or Dupont™'s Tyvek® paper (made of high density polyethylene fibers); or Dupont™'s Melinex® film/sheet (polyester); or Toray's Lumirror™ sheet (polyester).

15. The system of claim 1, wherein said portable or handhold air purification system has an electrical power management system to allow the system to work based on electric power from either a built-in rechargeable battery, or a USB connection, or a main electrical outlet.

16. The system of claim 1, wherein said portable or handhold air purification system has a device to measure and monitor the light intensity from said ultraviolet light source.

17. The system of claim 1, wherein said portable or handhold air purification system has an internal clock system to record total system-turn-on time or system usage time against a predetermined system lifetime for maintenance.

18. The system of claim 1, where said portable or handhold air purification system has a display method or an app (software) linked to its users' smart phone to provide a system health report and also give a warning for an incoming system maintenance.

19. The system of claim 6, where in said layer of photocatalyst nano particles is a layer of either Titanium dioxide (TiO2), or Zirconium oxide (ZrO), or Zinc oxide (ZnO), or Magnesium oxide (MgO), or tungsten trioxide (WO3), or the combinations of the above mentioned photocatalyst with or without addition of a small amount nano particles of a precious metal—either Pt, or Au, or Rd, or Rh, or Ru.

* * * * *